United States Patent
Amely-Velez

[11] Patent Number: 5,720,767
[45] Date of Patent: Feb. 24, 1998

[54] IMPEDANCE DEPENDENT IMPLANTABLE CARDIOVERTER-DEFIBRILLATOR

[75] Inventor: Jorge N. Amely-Velez, Simi Valley, Calif.

[73] Assignee: Pacesetter, Inc., Sylmar, Calif.

[21] Appl. No.: 720,738

[22] Filed: Oct. 2, 1996

[51] Int. Cl.$^6$ ............................................. A61N 1/39
[52] U.S. Cl. ................................... 607/5; 607/63
[58] Field of Search .................. 607/5, 7, 8, 63, 607/64

[56] References Cited

U.S. PATENT DOCUMENTS

| | | |
|---|---|---|
| 3,747,605 | 7/1973 | Cook. |
| 4,745,923 | 5/1988 | Winstrom. |
| 4,823,796 | 4/1989 | Benson. |
| 4,989,603 | 2/1991 | Carroll et al.. |
| 5,111,813 | 5/1992 | Charbonnier et al.. |
| 5,222,492 | 6/1993 | Morgan et al. ............... 607/5 |
| 5,350,403 | 9/1994 | Stroetmann et al. ............ 607/5 |
| 5,433,732 | 7/1995 | Hirsehberg et al. ............ 607/7 |
| 5,531,769 | 7/1996 | Fossan et al. ................. 607/5 |

*Primary Examiner*—Marvin M. Lateef
*Assistant Examiner*—George R. Evanisko

[57] ABSTRACT

An implantable cardiac stimulation device contains a high voltage defibrillating unit. A protection circuit is connected to the defibrillating unit to guard against excessive current during a high voltage discharge. The protection circuit prevents damage to the defibrillation unit and to the associated heart tissue. The defibrillation current is monitored by the protection circuit and if excessive, the defibrillation current is reduced by routing the current through an additional impedance. The protection circuit operates in realtime to remove the additional impedance if the defibrillation current returns to a safe level. A memory device attached to the protection circuit records the event of an excessive defibrillation current.

25 Claims, 4 Drawing Sheets

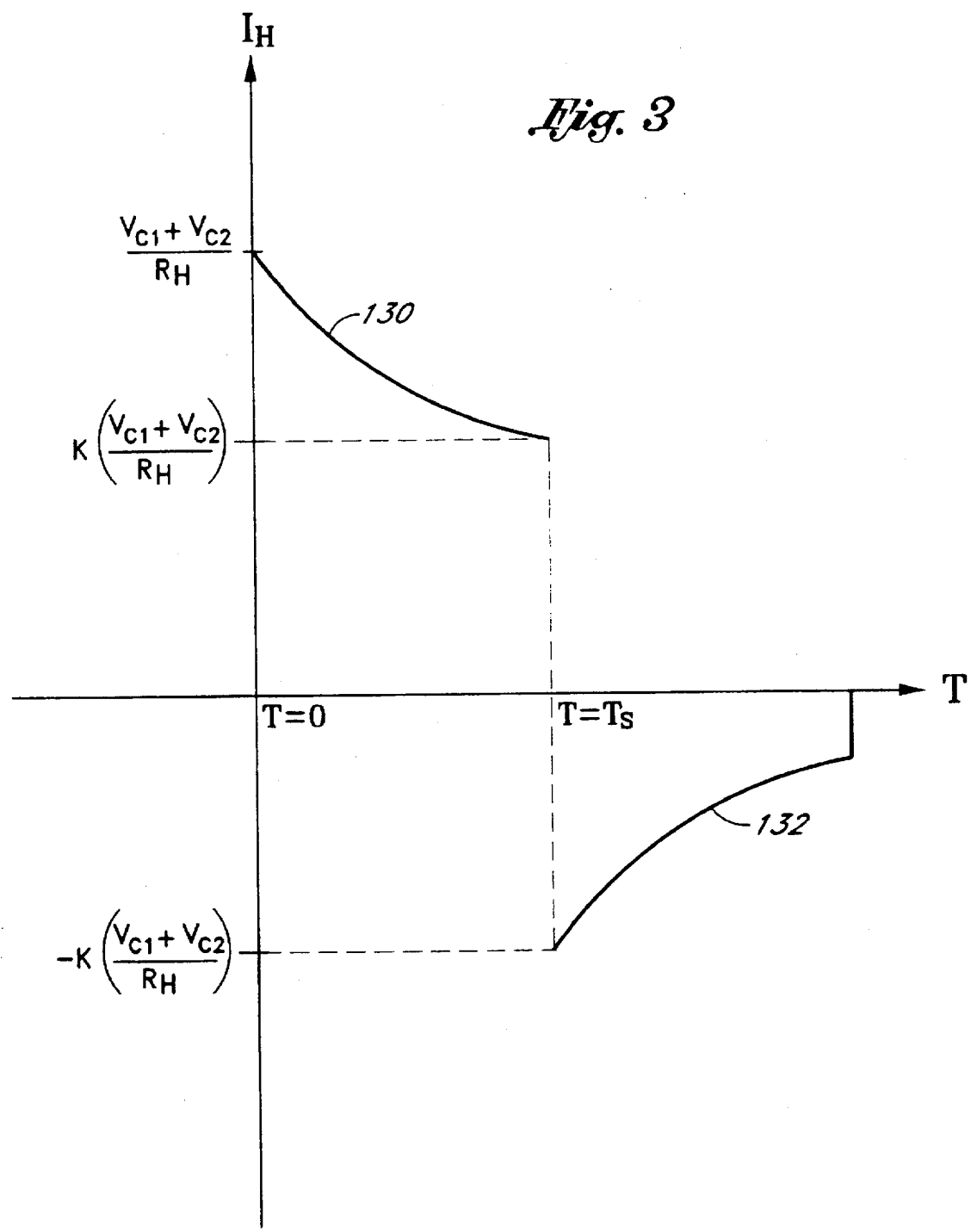

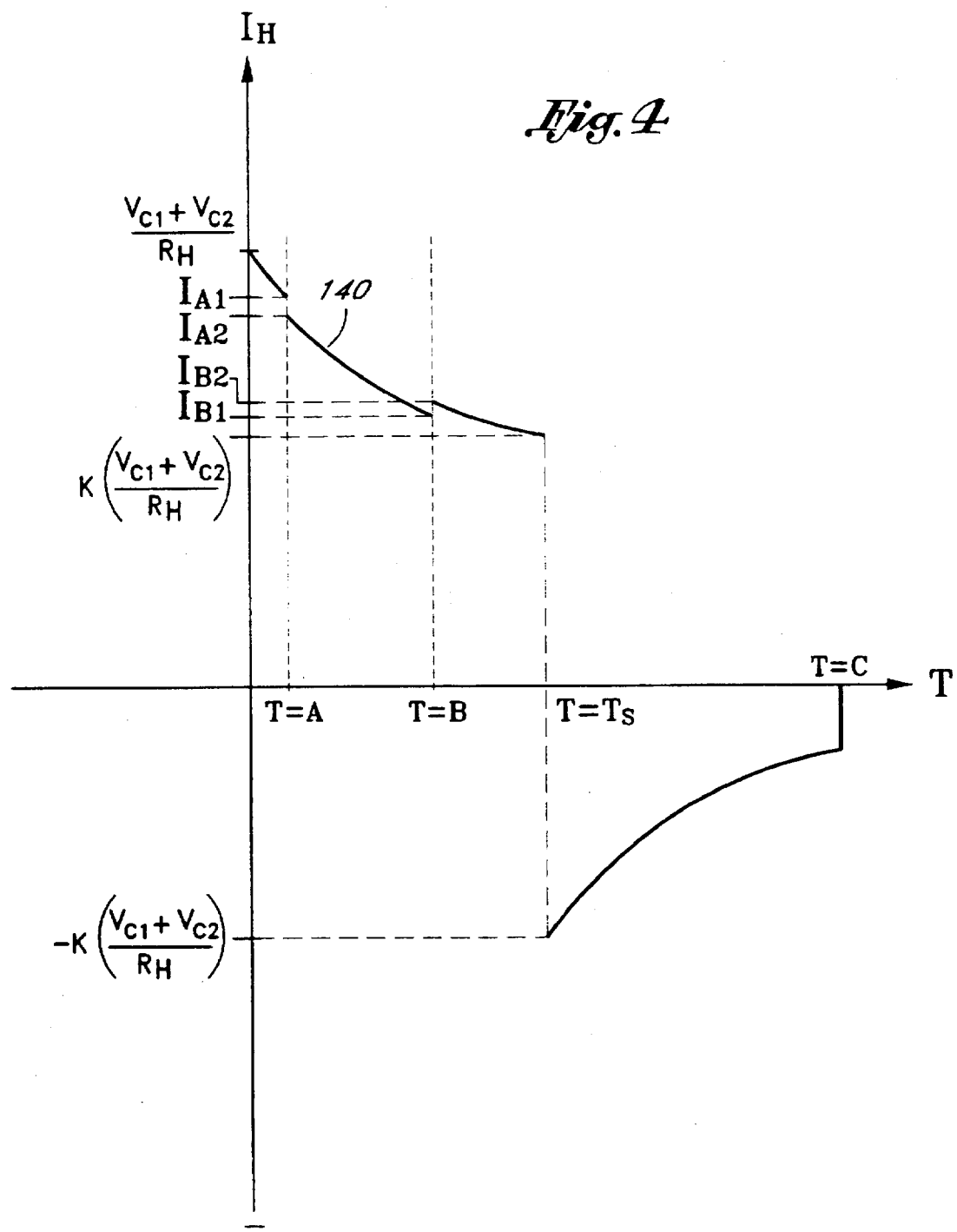

IMPEDANCE DEPENDENT IMPLANTABLE CARDIOVERTER-DEFIBRILLATOR

FIELD OF THE INVENTION

This invention relates generally to circuit protection devices, and especially those designed to limit the flow of current. More particularly, this invention relates to apparatus and methods for limiting the flow of current from an implantable cardioverter-defibrillator during a high-voltage discharge to the heart of a patient.

BACKGROUND OF THE INVENTION

Implantable cardioverter-defibrillators (ICDs) are now routinely used within patients who have abnormally rapid cardiac activity. These defibrillators apply high-voltage pulses directly to the heart when abnormally high heart rate activity is detected. The rapid heart rate which triggers a high voltage discharge can be sensed by the ICD sensing circuitry. Many ICDs also include cardiac pacing circuitry to control abnormally slow heart rates.

During operation of a typical ICD, cardiac rate is monitored by the sensing circuitry, and low-voltage electrical pulses are used to control an abnormally slow heart rate. When the heart rate is abnormally high, for example if the heart begins to fibrillate, the ICD will discharge a high-voltage pulse to the heart in an attempt to normalize cardiac activity. Such high-voltage pulses can be as large as 800 volts and are typically 5-20 milliseconds in duration. The current delivered by such a high-voltage shock is inversely proportional to the impedance of the heart.

Cardiac impedances vary between 20-80 ohms, depending on the patient and the lead system used for shock delivery to the heart. Other factors can also affect the value of a patient's cardiac impedance as seen by an ICD. For example, the positional placement of the defibrillation leads on or in the heart can vary the impedance between the leads. Accordingly, most ICDs are designed to withstand the level of current resulting from a high-voltage discharge to a 20-ohm cardiac load.

Many ICDs are programmable, allowing an attending physician to adjust the level of voltage discharged during a defibrillation episode. The programmed voltage is based upon an assumed value of a patient's cardiac impedance. If the patient's cardiac impedance is less than predicted, a voltage discharge may transmit excessive and potentially dangerous current through the patient and through the ICD. Such excessive current levels are obviously undesirable, and if observed, the level of voltage delivered to a patient's heart should be reprogrammed to reduce the amount of transmitted current. Unfortunately, determination of the presence of an excessive current condition may occur only after the ICD has been discharged and the excessive current has been transmitted. Thus, there is a risk that the circuitry of the ICD or a patient's cardiac tissue may already be damaged from the high voltage ICD discharge.

It is possible that an attending physician may know the actual cardiac impedance of a patient's heart before installation of an ICD unit. With such information, the high-voltage potential delivered by the ICD can be adjusted to accommodate for the impedance value of the heart. Even with such pre-implant adjustments, however, the cardiac impedance for a particular patient, as seen from the output leads of a defibrillator, can fluctuate. With such fluctuations, a preset defibrillation voltage level may create a current surge large enough to damage the ICD or injure the patient. A damaged ICD unit is highly undesirable because it exposes the patient to a life-threatening risk from failure to treat arrhythmias, and risk from the concomitant surgery required to replace a damaged unit.

Attempts have been made in the prior art to regulate parameters relating to the level of current in a defibrillation system. For example, in U.S. Pat. No. 5,111,813, issued to Charbonnier et al., an external defibrillation system normalizes the defibrillation current flowing through the transthoracic impedance of a patient. The apparent objective of the Charbonnier device is to lower the discharge voltage across a low transthoracic impedance, while still providing adequate current to excite the heart. According to Charbonnier, normalizing the defibrillation current helps ensure that sufficient current will be administered to the patient, avoiding the necessity of subsequent defibrillation attempts.

U.S. Pat. No. 4,745,923, issued to Winstrom, discloses one method for limiting current flow to a pacemaker in response to defibrillation pulses from an associated defibrillator. To inhibit excessive current, a protection circuit is placed in the path of one of the leads of the pacing device. The protection circuit has a low impedance path and a high impedance path operated by a switching mechanism. When the current through the protection circuit exceeds a predetermined level, the current is routed through a high impedance path of the protection circuit in order to dissipate the energy.

Other attempts have been made in the prior art to protect against excessive current in a pacemaker device including U.S. Pat. No. 4,440,172, issued to Langer; and U.S. Pat. No. 3,886,932, issued to Suessmilch. None of these devices, however, provides adequate protection against large currents in a defibrillation device. Nor do the devices found in the prior art prevent current oscillation which can occur from the switching of impedance paths during a defibrillation discharge. Accordingly, there is a need in the art for a protection circuit to prevent the flow of excessive current from damaging an ICD unit and associated heart tissue. There is also a need in the art for such a protection circuit which is integrated within the ICD housing.

SUMMARY OF THE INVENTION

In accordance with a preferred embodiment, an ICD device has an integrated protection circuit for limiting excessive current from flowing through the ICD. The protection circuit has a sensor which determines the level of current flowing through a patient's heart during a high-voltage discharge. The sensor operates in real-time in order to increase the impedance of the discharge path to a level which reduces the current flow and correspondingly, the high-voltage discharge rate. The added impedance is sufficient to reduce the current to acceptable tolerance levels of the ICD while maintaining adequate current to produce the desired cardiac response. Once the discharge current has fallen below an acceptable level, the sensor triggers removal of the added impedance to allow for normal operation of the ICD. Subsequent defibrillation discharges will again be monitored by the sensor to detect excessive current. The sensor device will operate in connection with either a monophasic or biphasic defibrillation discharge.

Information pertaining to the defibrillation discharge, including information indicating whether an excessive current was detected by the sensor, may be stored for later analysis. This information may be transmitted to an internal pacing device, or it may be downloaded by an attending physician to an external programming unit. The attending physician may then make adjustments to the programmed defibrillation voltage based on the stored data.

The ICD unit disclosed herein thus aids medical personnel in preventing damage to an ICD unit, or injury to a patient, by curtailing excessive defibrillation current. This prevents subsequent surgical procedures to repair a damaged ICD. In addition, the physician may reprogram the discharge-voltage level of a defibrillator reducing the likelihood of damage to the ICD in the future.

BRIEF DESCRIPTION OF THE DRAWINGS

The above and other aspects, features, and advantages of the present invention will be more apparent from the following particular description thereof presented in conjunction with the following drawings, wherein:

FIG. 3 is a graphical representation of a typical discharge current during a defibrillation episode which has not exceeded a predetermined value.

FIG. 4 is a graphical representation of a discharge current during a defibrillation episode which has exceeded a predetermined value and has been adjusted in accordance with a preferred embodiment.

DETAILED DESCRIPTION OF THE PREFERRED EMBODIMENT

Figure 1:
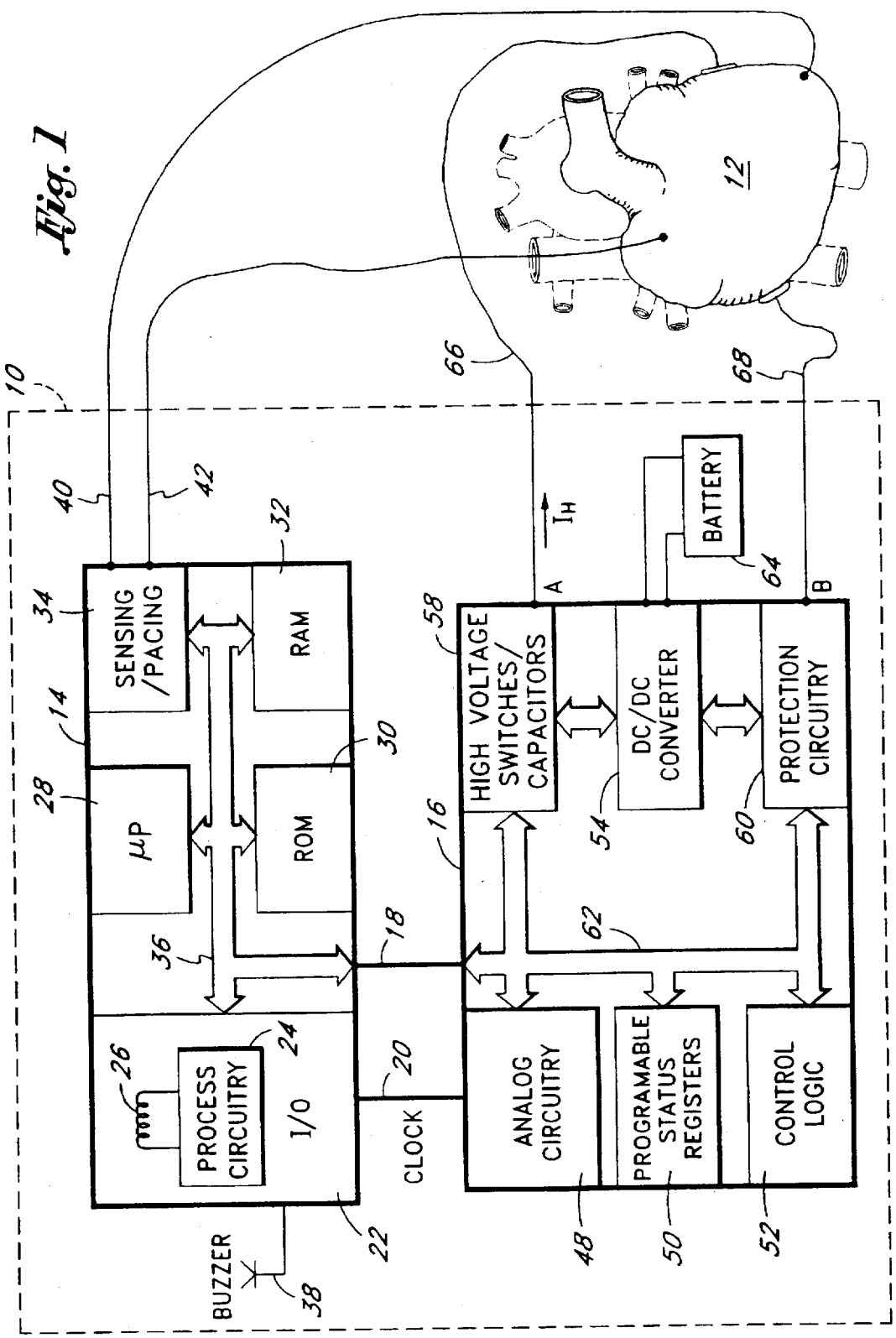
FIG. 1 is a schematic block diagram of a pacing device and a cardioverter-defibrillator operatively connected to a heart for controlling a high-voltage output current.

Referring initially to FIG. 1, a cardiac stimulation device 10, in block diagram form, is electrically connected to a heart 12 of a patient (not shown). The implantable cardiac stimulation device 10 of FIG. 1 comprises a controller 14 connected to a defibrillating unit 16 via a communication port 18. The port 18 may be serial path or a parallel connection. A signal path 20 transmits a synchronous clock signal between the controller 14 and the defibrillator 16.

The controller 14 contains an input/output device 22 having process circuitry 24 attached to an internal antenna 26 for sending and receiving data between the device 10 and an external programming unit (not shown). The process circuitry 24 performs the necessary signal conversion in order to transmit and receive digital data. Also contained in the controller 14 is a microprocessor 28, memory units 30 and 32, and sensing/pacing circuitry 34. The internal components of the controller 14 communicate via a bus 36. A piezoelectric device 38 is connected to the controller 14 for providing audible information to a patient relating to cardiac events. Sensing/pacing leads 40 and 42 are connected to the heart 12 for regulating everyday cardiac activity. The leads 40, 42 are inserted into the heart 12 in a manner common to one of ordinary skill in the art.

The defibrillating unit 16 contains analog circuitry 48, programmable/status registers 50, control logic 52, a DC to DC converter 54, high voltage discharge capacitors and associated high power switches 58, and protection circuitry 60. All of the components 48, 50, 52, 54, 58, and 60 are interconnected via communication bus 62. An internal battery 64 is connected to the DC to DC converter 54 to provide the necessary charge needed for a heart defibrillation discharge. High voltage defibrillation leads 66 and 68 are connected to opposite sides of the heart 12 as shown. Lead 66 is a high voltage, or transmission lead, which is connected between the heart 12 and the high power switches 58. Lead 68 is a return lead connected between the heart 12 and the protection circuitry 60. Leads 66 and 68 may be sewn to an exterior portion of the heart using patches or they may be placed transvenously within the heart.

In operation of the cardiac stimulation device 10, the controller 14 monitors normal rhythmic cardiac functions of the heart 12 via pacing/sensing leads 40 and 42. Specifically, upon detection of a low heart rate by the sensing/pacing circuitry 34, a low voltage electrical pulse is transmitted along leads 40 and 42 to increase heart rate to its physiologic range. If leads 40 and 42 sense abnormally high rates, the controller 14 will instruct the defibrillating unit 16 to deliver a high voltage shock to the heart 12. As can be appreciated by one of ordinary skill in the art, the interaction between the controller 14 and the defibrillator 16, along the communication port 18, will be determined based on internal programming instructions present in the controller 14.

In accordance with a preferred embodiment of the present invention, the protection circuit 60 is contained within the defibrillation unit 16. The protection circuit 60 is advantageously connected to guard against damage to the defibrillation unit during a high voltage discharge. It can be appreciated that various implementations of a cardiac stimulation device can be employed which make use of the protection circuit 60. Moreover, the protection unit 60 may be configured externally to the actual defibrillator 16.

A high voltage discharge transmitted through the high power switches 58, will produce a large current, $I_H$, through lead 66. Defibrillation voltages will be dependent on the programming for the stimulation device, but they can reach values on the order of 800 volts. The value of the current $I_H$ resulting from the discharge voltage will be dependent upon the impedance of the heart muscle 12, the particular leads used, and any other impedances present in the discharge pathway. Although previous attempts have been made to protect pacemakers from a high voltage discharge of a defibrillator, such attempts do not offer any protection for the defibrillator itself.

The preprogrammed discharge voltage of a typical defibrillating unit for a particular patient is a function of the patient's measured defibrillation threshold for the lead system that is used. The impedance of a typical heart muscle will normally range between 20–80 ohms. Accordingly, large currents are created from a high voltage discharge through the heart. Also, because the impedance is small in relation to the discharge voltage, slight variances in the impedance can cause large changes in resulting current. For example, a 500 volt shock discharge through an 80 ohm load creates an initial current of 6.25 amps. The same voltage discharged through a 20 ohm load creates an initial current of 25 amps.

Excessive currents present in the high voltage discharge circuitry pose a serious hazard to the patient both directly and indirectly. Specifically, large currents flowing through the heart create the risk of tissue damage to the organ itself, directly injuring the patient. A large current which only damages the defibrillation unit poses the indirect risk to the patient of malfunction during a subsequent defibrillation discharge. In addition, a defective defibrillator must be replaced exposing the patient to an otherwise unnecessary surgery.

Figure 2:
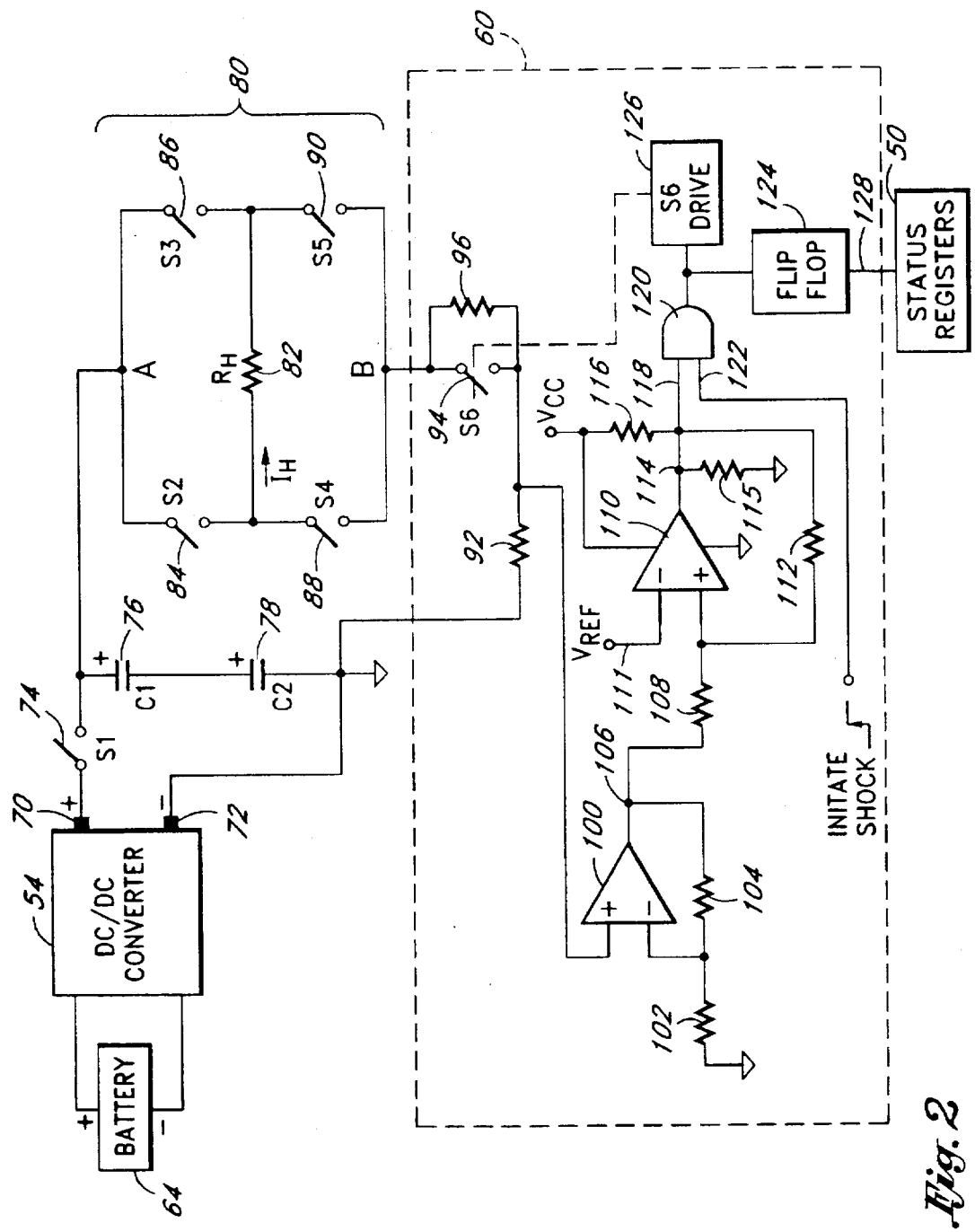
FIG. 2 is a schematic diagram of a protection circuit and associated circuitry of a cardioverter-defibrillator in accordance with a preferred embodiment.

FIG. 2 is a schematic representation of a portion of the defibrillating unit 16 (shown in FIG. 1). In particular, the battery 64 is shown connected to the DC to DC converter 54 having a positive output terminal 70 and a negative output terminal 72. A high power switch 74 is connected between the terminal 70 and one end of a high voltage capacitor 76. The capacitor 76 is connected in series to a second high voltage capacitor 78. The capacitors 76 and 78 are connected in series between the switch 74 and the terminal 72. A positive terminal of the capacitor 76 is connected to one end of a switching network 80 for delivering a high voltage discharge from the capacitors 76 and 78 through a heart muscle represented by a resistor 82. Specifically, the positive terminal of the capacitor 76 is connected to one end of high power switches 84 and 86 at a node A which are in turn connected to opposite ends of the resistor 82. The resistor 82 is also connected at opposite ends to high power switches 88 and 90 such that one end of the switch 84 is connected to one end of the switch 88 and one end of the switch 86 is connected to one end of the switch 90. An opposite end of the switch 88 and an opposite end of the switch 90 are connected together at a node B to form the switching network 80 around the resistor 82.

The protection circuitry 60 is connected between the node B and the terminal 72 for detecting when the current through the resistor 82, $I_H$, is undesirably high. The protection circuit 60 is designed to compensate for such excessive current. The circuit 60 comprises a current sensing resistor 92 connected between the terminal 72 and a first end of a high power switch 94. A second end of the switch 94 is connected to node B and a resistor 96 is connected in parallel with the switch 94. Accordingly, the capacitors 76 and 78 are connected across the series-connected combination of the network 80, the switch 94 and the resistor 92.

Before discussing the protection circuitry in detail, a discussion of a typical defibrillation discharge is in order. The circuit of FIG. 2 operates as a biphasic discharge device for delivering a positive and negative electric current through a patient's heart muscle.

In preparation of a high voltage discharge to the heart, and in response to an appropriate command from the microprocessor 28, the DC to DC converter 54 first steps up the voltage from the battery 64. The high voltage capacitors 76 and 78 are then charged to the preprogrammed level. During such a charge, the switch 74 is closed while the switches 84, 86, 88 and 90 are open. Then, upon receipt of a signal from the microprocessor to initiate the high voltage shock, switches 84 and 90 are closed while switches 86 and 88 remain open. This results in a positive discharge current $I_H$ flowing through the resistor 82 and through switches 84 and 90. Once the voltage across the capacitors 76 and 78 has decayed a predetermined amount, which may be on the order of 60%, the switches 84 and 90 are opened while the switches 86 and 88 are closed. As a result, the current $I_H$ becomes negative flowing in the opposite direction through the resistor 82 to complete the defibrillation discharge. This switching action produces the biphasic pulse through the heart impedance 82.

Referring again to the protection circuit 60 of FIG. 2, it can be appreciated that the level of current flowing through the resistor 82 will equal the current flowing through the sensing resistor 92. This creates a voltage across the resistor 92 which is fed to the non-inverting terminal of an operational amplifier 100. The amplifier 100 is configured as a non-inverting amplifier having an inverting terminal connected through a resistor 102 to ground, and also connected through a resistor 104 to an output 106. In a preferred embodiment, the value of the resistor 92 is small, i.e., less than one ohm. Accordingly, the relatively small voltage across the resistor 92 is sensed and amplified by the amplifier 100 depending on the value of the resistors 102 and 104.

The output 106 is fed into a non-inverting comparator circuit with hysteresis. Specifically, a resistor 108 is connected between the output 106 and a non-inverting input of an amplifier 110. The amplifier 110 is configured as a comparator having an inverting terminal 111 connected to a reference voltage, $V_{Ref}$. The non-inverting terminal is connected through a resistor 112 to an output 114 of the amplifier 110. The output 114 of the amplifier 110 is biased to the amplifier's supply voltage, $V_{cc}$, through a pull-up resistor 116. A load resistor 115 is connected between the output 114 and ground potential.

The output 114 of the amplifier 110 is connected to an inverting terminal 118 of an "AND" logic gate 120. A second input 122 of the AND gate 120 is connected to a lead for receiving a logic signal INITIATE SHOCK, which indicates the initiation of a high voltage discharge pulse through a patient's heart. The logic output of the AND gate 120 connects to a memory device 124. The memory device 124, which may be constructed as a D flip-flop, has an output 128 which is ultimately connected to the registers 50 of the stimulation device. The output of the AND gate 120 is also connected to a drive unit 126 which is in turn operatively connected to the high power switch 94.

In operation, the protection circuit 60 first senses the current $I_H$ flowing through the resistor 82, which is the same as that flowing through the associated defibrillator 16 (shown in FIG. 1). The current, $I_H$, creates a voltage drop across the resistor 92 which is measured and amplified by the amplifier 100. The resultant amplified voltage appearing at the output 106 is fed into the non-inverting input of the amplifier 110. The level of amplification provided by the amplifier 100 should be set as a function of the anticipated voltage drop across the resistor 92 in order to provide the desired operation of the amplifier 110, as described below.

The amplifier 110 is configured as a non-inverting comparator with hysteresis. The hysteresis of the amplifier 110 is defined as the difference in the input voltage level which causes the output to switch to a logic high level, measured against the input voltage level which causes the output to switch to a logic low level. In operation, the output 114 of the amplifier 110 will rise to a high logic state when the voltage at the output 106 exceeds a predetermined value, $V_1$. The desired predetermined value, $V_1$, will be dependent upon the defibrillation threshold and the acceptable current levels for $I_H$. The voltage level, $V_1$, which is required to cause a change in the output 114, can be varied by adjusting the values of the resistors 108, 112, and the reference voltage appearing at the inverting input 111.

If the output 114 has reached a high logic state, this indicates that the current $I_H$ has reached a predetermined level which is deemed unacceptable. The AND gate 120 controls the switch drive 126 for the switch 94. The INITIATE SHOCK signal is activated to a high logic state only when a high voltage discharge to the heart occurs. Accordingly, when a high voltage discharge is not occurring, the output of the gate 120 will always remain at a low logic state. When the gate 120 is at a low logic state, the switch 94 will remain closed shorting out the resistor 96. As can be appreciated by one of ordinary skill in the art, the control circuit for the switch 126 can operate with positive or negative logic, as long as the switch 126 is in the normally closed state during periods of acceptable $I_H$ current levels.

The output of the AND gate 120 will change to a high logic level when its two inputs are positive, i.e., when a high voltage discharge is occurring and when the current $I_H$ exceeds a predetermined value. When this occurs, the switch 94 is opened in response to a signal sent to its respective drive circuit 126 from the gate 120. As a result, the current $I_H$ flows through a higher impedance path which includes the resistor 96.

Once the output 114 has reached a high logic state, the output 114 will not return to a low logic state until the voltage at the non-inverting input decreases to a certain level, $V_2$, which is below the level $V_1$. The difference in these voltage levels, $V_{hys}$ (where $V_{hys}=V_2-V_1$), is the hysteresis voltage and is calculated in accordance with the following equation $V_{hys}=V_{cc}(R_{108}/R_{112})$. A full operational specification of a comparator with hysteresis can be found in National Semiconductor's Application Note 74, pages 256–260, describing "A Quad of Independently Functioning Comparators", which document is incorporated herein by reference. As will be explained in more detail in connection with FIG. 4, use of a non-inverting comparator with hysteresis is advantageous because it avoids oscillation which can occur when switching the resistance path of the current $I_H$.

Opening of the switch 94 adds additional impedance to the defibrillator load by inserting the resistor 96 in series with the heart muscle. This protects the high voltage circuitry of the defibrillator, and the heart muscle, by automatically decreasing the current through the heart when it reaches a high level. In a preferred embodiment, the resistor 96 may have a value of approximately 10–12 ohms. This value ensures that the decrease in current level will be significant enough to have a protective effect, yet small enough to deliver adequate defibrillation current to the heart. The protection circuit 60 disclosed herein may even be modified to include multiple impedance levels instead of the single-value resistor 96. In such a configuration, one of the multiple impedance levels would be added to the discharge circuit depending upon the amount of current flowing through the heart.

The drive circuit 126 can be implemented using various methods common to one of ordinary skill in the art. However, in a preferred embodiment such drive circuits are constructed of solid-state transistor technology to ensure switching times which are fast enough to have an immediate protective effect on the current level $I_H$. Acceptable solid-state devices include insulated gate bipolar transistors (IGBTs) such as those made by IXYS and sold under the designation IXGH10N100.

The output of the AND gate 120 is connected to the memory device 124 to record the occurrence of high current levels. The output 128 of the memory device 124 is connected to the registers 50. In addition to various discharge circuit parameters, the registers 50 store and retain information pertaining to the detection of excessive current levels of $I_H$. This information may be accessed by the microprocessor 28 (shown in FIG. 2) for analysis and further transmission to an external programming unit. The information stored by the memory unit 124, and transferred to the registers 50, may include the degree, amount, and/or frequency of high-current events which trip the switch 94. Access to this information is vital to an attending physician. Specifically, a physician may wish to alter the programmed discharge voltage to protect the patient's heart, and the internal stimulation device 10, from damage.

Because the protection circuit 60 operates continuously to prevent the flow of excessive current through the heart muscle, its use offers the distinct advantage of protecting against damage during an initial high voltage discharge. Moreover, the circuit 60 can provide feedback indicating when dangerous current levels are present, while simultaneously operating to reduce such current levels.

In a preferred embodiment, the circuit 60 operates in real-time to add or remove a resistive load to the heart discharge circuitry. The real-time operation results from the constant monitoring by the amplifier 100 of the voltage across the sensing resistor 92. The amplifier 110 in turn continuously operates the switch 94. The effect on current flow from the real-time operation of the switch 94 can best be seen in conjunction with FIGS. 3 and 4.

FIG. 3 is a graphical representation of time versus current during a high voltage discharge through the heart muscle. During the discharge represented in FIG. 3, the switch 94 remains closed the entire time of the discharge indicating that the current level did not reach a predetermined unacceptable level. Accordingly, the rate of decay is that which occurs as the voltage across the capacitors 76 and 78 (shown in FIG. 2), i.e., $V_{C1}+V_{V2}$, is discharged through the resistor 82 (shown in FIG. 2). Initially, at the time of T=0, a maximum current of level $I_H=(V_{C1}+V_{C2})/R_H$ is delivered through the heart muscle while the switches 86 and 88 (shown in FIG. 2) are opened and the switches 84 and 90 (shown in FIG. 2) are closed. The value of $I_H$ will begin to decrease, represented by the curve 130, as the voltage across the capacitors 76 and 78 discharges. Once the current level reaches a portion of its original value at time $T=T_S$, e.g., $K(V_{C1}+V_{C2})/R_H$, the switches 84 and 90 will open and the switches 86 and 88 will close. This switching action reverses the flow of current through $R_H$ such that $I_H$ is represented by $-K(V_{C1}+V_{C2})/R_H$. The level of current $I_H$ will continue to decrease as represented by the curve 132.

FIG. 4 is a graphical representation of time versus current during a high voltage discharge through the heart muscle where the current $I_H$ exceeds an acceptable predetermined level. During the discharge represented in FIG. 4, the switch 94 will temporarily open adding a resistive load in the current path of $I_H$ to decrease the level of $I_H$. This event occurs in FIG. 4 at the time T=A. Optimally, the delay in sensing and reducing an excessive current, represented in FIG. 4 by the distance between time T=0 and T=A, will be as small as possible to minimize the risk of damage from the current. Typically, the time of T=A will be measured in microseconds.

As seen in FIG. 4, the current $I_H$ changes from a value of $I_{A1}$ to a reduced value of $I_{A2}$ upon insertion of resistor 96 (shown in FIG. 2) in the path of $I_H$. The current $I_H$ then continues to decrease along a curve 140 as the capacitors 76 and 78 (shown in FIG. 2) continue to discharge. During the period between time T=A and T=B, however, the time constant for the discharge circuit is altered from insertion of the series resistor 96. As a result, the decay rate of the current and discharge voltage will be slightly less during the A-B time interval than during the B-$T_S$ time interval.

At time T=B, the current $I_H$ reaches a level $I_{B1}$. At this level, the protection circuit 60 operates to remove the added resistor 96 by closing the switch 94. This causes a slight increase in the current $I_H$ to a new and safe level $I_{B2}$. The current $I_H$ then decreases in the manner described in connection with FIG. 3. Once the capacitor has been substantially discharged, in this case at time T=C, the switches 86 and 88 (shown in FIG. 2) are both opened to stop further discharge. At time T=C, most of the energy stored in the discharge capacitors has been delivered to the heart in a fairly short amount of time.

The discharge time for a typical cardioverter-defibrillator is approximately 8–20 milliseconds. The circuit 60 can be designed so that current levels $I_{A1}$, $I_{A2}$, $I_{B1}$, and $I_{B2}$ meet the needs of a particular patient or a particular cardiac stimulation device. For example, the inputs to the amplifiers 100 and 110 can be biased, through selection of the resistor values 102, 104, 108, and 112 (shown in FIG. 2), to dictate what current level of $I_H$ will activate the switch 94. The associated threshold voltage will be based upon acceptable medical criteria pertaining to defibrillation current levels. The threshold voltage and current levels may also be determined from tolerance characteristics of switching elements, and other circuit elements, that can be damaged by the flow of a large current.

A preferred embodiment of the present invention is constructed in accordance with a biphasic pulse circuit. It can be appreciated, however, that the same protection circuit disclosed herein is equally applicable to a defibrillation unit which discharges a monophasic pulse. Also, one of ordinary skill in the art can also appreciate that the system disclosed herein for providing protection against high current levels can be applied to a defibrillator unit 16 which is not integrally constructed with an associated controller 14.

Through the foregoing description and accompanying drawings, the present invention has been shown to have important advantages over current implantable cardiac stimulation devices. While the above detailed description has shown, described, and pointed out the fundamental novel features of the invention, it will be understood that various omissions and substitutions and changes in the form and details of the device illustrated may be made by those skilled in the art, without departing from the spirit of the invention. Therefore, the invention should be limited in its scope only by the following claims.

What is claimed is:

1. An apparatus for regulating the high voltage discharge of an implantable cardioverter-defibrillator having an output lead affixed to a first portion of the heart of a patient and a return lead affixed to a second portion of the heart comprising:
   means for selectively discharging a high voltage potential to the output lead in response to fibrillation of the heart whereby a discharge current flowing through the output lead is a function of an impedance connected across the high voltage potential;
   means for generating a signal in response to a level of the discharge current;
   means for preventing oscillation of the discharge current when the discharge current exceeds a predetermined value; and
   means for adjusting the level of the discharge current so that a lowered level of discharge current flows through the heart in response to the signal.

2. The apparatus of claim 1, wherein the means for adjusting comprises a resistor and a switching element having a first state and a second state, the resistor being non-conductive when the switching element is in the first state, and the resistor being conductive when the switching element is in the second state.

3. The apparatus of claim 2, wherein the switching element remains in the first state when the discharge current is less than a predetermined level and the switching element enters the second state when the discharge current exceeds the predetermined level.

4. The apparatus of claim 2, wherein the switching element is a solid state transistor circuit.

5. The apparatus of claim 2, wherein the switching element is biased to remain in the first state when the signal is below a predetermined level.

6. The apparatus of claim 2, further including means for indicating when the switching element has entered the second state.

7. The apparatus of claim 6, wherein the indicating means comprises a memory circuit capable of storing information indicative of the number of times the switching element has entered the second state.

8. The apparatus of claim 1, wherein the adjusting means comprises a conductive element having a plurality of selectable impedance levels, a plurality of switching elements, and means for connecting at least one of the impedance levels in series with the output lead in response to the signal.

9. The apparatus of claim 1, wherein the adjusting means comprises a device for inserting an impedance in the path of the output lead when the discharge current exceeds a predetermined amount.

10. The apparatus of claim 1, wherein the adjusting means comprises an impedance element and a switch, the switch having a first state to bypass the transmission of current from the high voltage discharge through the impedance element, and a second state to permit transmission of current through the impedance element.

11. The apparatus of claim 1, wherein the means for preventing oscillation comprises an amplifier configured as a comparator with hysteresis for preventing oscillation of the discharge current when the discharge current exceeds a predetermined value.

12. The apparatus of claim 1, wherein the means for adjusting occurs in real-time to automatically affect the discharge current in response to the signal.

13. The apparatus of claim 1, wherein the means for generating generates a first signal for reducing the discharge current when the discharge current exceeds a first predetermined value, and generates a second signal for increasing the discharge current when the discharge current falls below a second predetermined value.

14. A cardiac stimulation device for delivering a high-voltage electric stimulus to a heart of a patient comprising:
   a charging circuit capable of generating and storing a high-voltage electric stimulus;
   a delivery circuit connected to the charging circuit to deliver the high-voltage electric stimulus to the heart, the delivery circuit having a first conductive path through the heart with a first impedance for transferring a current of the high-voltage electric stimulus, and having a second conductive path through the heart with a second impedance greater than the first impedance;
   a protection circuit connected to the delivery circuit to regulate the high voltage electric stimulus, the protection circuit channeling the current through the first conductive path when the current is below a predetermined value and channeling the current through the second conductive path when the current is above a predetermined value; and
   means connected to the protection circuit for storing data representative of the current level flowing through the heart when the high voltage electrical stimulus is delivered.

15. The cardiac stimulation device of claim 14, wherein the protection circuit comprises a switch for creating the first and second conductive paths, a drive circuit for activating the switch, the drive circuit having a comparator to sample the current and generate a signal representing the level of the current.

16. The cardiac stimulation device of claim 15, wherein the comparator has a positive input lead connected to an amplifier, a negative input terminal connected to a reference voltage, and an output terminal connected to a logic gate for generating a logic output for activating the switch.

17. The cardiac stimulation device of claim 14, wherein the means for storing the data is a solid-state memory device.

18. The cardiac stimulation device of claim 14, wherein the charging circuit includes two capacitors connected to a DC/DC converter.

19. A method of protecting the high voltage output stage on an implantable cardioverter-defibrillator comprising:

providing an implantable cardioverter-defibrillator having a high-voltage storage capacitor and a conducting lead connected to a heart of a patient for administering a current therethrough;

charging the high-voltage storage capacitor with a predetermined defibrillation voltage level;

discharging the high-voltage storage capacitor causing the current to flow through the heart in response to an activation instruction generated by the cardioverter-defibrillator;

monitoring a signal indicative of the level of the current flowing through the heart;

inserting an impedance in series with the flow of the current through the heart when the signal exceeds a predetermined value; and storing data within a memory unit of the cardioverter defibrillator, the data indicating whether the signal has exceeded the predetermined value.

20. The method of protecting the high voltage output stage of an implantable cardioverter-defibrillator of claim 19 further comprising the step of storing data within a memory unit of the cardioverter-defibrillator, the data indicating the number of occurrences that the signal has exceeded the predetermined value.

21. The method of protecting the high voltage output stage of an implantable cardioverter-defibrillator of claim 19 further comprising a second lead connected between the cardioverter-defibrillator and the heart for conducting the flow of the current therethrough.

22. The method of protecting the high voltage output stage of an implantable cardioverter-defibrillator of claim 19 wherein the signal is created by comparing a reference voltage level with a sensed voltage level proportional to the current level.

23. The method of protecting the high voltage output stage of an implantable cardioverter-defibrillator of claim 19 further comprising the step of removing the impedance from the flow of current through the heart when the signal is less than the predetermined value.

24. The method of protecting the high voltage output stage of an implantable cardioverter-defibrillator of claim 19 further comprising the step of removing the impedance from the flow of current through the heart when the signal is at least a preselected fixed amount less than the predetermined value.

25. The method of protecting the high voltage output stage of an implantable cardioverter-defibrillator of claim 24 wherein the fixed amount is a hysteresis voltage determined as a function of a defibrillation threshold for the heart of the patient.

* * * * *